(12) United States Patent
Vandenbergh et al.

(10) Patent No.: US 6,277,374 B1
(45) Date of Patent: Aug. 21, 2001

(54) **PROCESS FOR PRODUCING BY CULTURING *LACTOBACILLUS CASEI* VAR. *RHAMNOSUS* YEAST AND MOLD INHIBITING PRODUCTS**

(75) Inventors: Peter A. Vandenbergh, Sarasota, FL (US); Stephen W. King, Napa, CA (US)

(73) Assignee: Microlife Technics, Inc., Hoffman Estates, IL (US)

( * ) Notice: Subject to any disclaimer, the term of this patent is extended or adjusted under 35 U.S.C. 154(b) by 0 days.

(21) Appl. No.: 09/314,370

(22) Filed: May 19, 1999

Related U.S. Application Data

(62) Division of application No. 07/905,132, filed on Jun. 23, 1992, now Pat. No. 5,965,414, which is a continuation of application No. 07/468,575, filed on Jan. 23, 1990, now abandoned, which is a continuation of application No. 07/082,118, filed on Aug. 6, 1987, now abandoned, which is a continuation-in-part of application No. 06/794,468, filed on Nov. 4, 1985, now Pat. No. 4,956,177.

(51) Int. Cl.$^7$ .................................................. A61K 35/74
(52) U.S. Cl. ........................... 424/115; 424/114; 424/170
(58) Field of Search ..................................... 424/115, 114, 424/170

(56) References Cited

U.S. PATENT DOCUMENTS 3,689,640  9/1972  Shahani et al. .
4,956,177  9/1990  King .

FOREIGN PATENT DOCUMENTS 8001045  8/1980  (NL) .
1109436  8/1984  (SU) .

OTHER PUBLICATIONS

Vincent et al., J. Bacteriol. vol. 78, pp 477–484 (1959).
ATCC Catalogue of Bact. pp. 115–118 (1989).
Rehm et al., "Biotechnology" vol. 5, p 73 (1983).
Condensed Chemical Dictionary p 502 (1974).
The Merck Index, p 768 (1983).
Dairy Microbiology, pp. 355–360 (Prentice Hall, Inc. 1957).

*Primary Examiner*—Irene Marx
(74) *Attorney, Agent, or Firm*—Ian C. McLeod

(57) ABSTRACT

A method for producing a novel yeast and mold inhibiting products (FIC) from a Lactobacillus, particularly a *Lactobacillus casei* having the yeast and mold producing characteristics of *Lactobacillus casei* var. *rhamnosus* NRRL-B-15972 is described. The products (FIC) are particularly useful in retarding yeast and mold growth in foods and other materials in need thereof.

21 Claims, No Drawings

PROCESS FOR PRODUCING BY CULTURING *LACTOBACILLUS CASEI* VAR. *RHAMNOSUS* YEAST AND MOLD INHIBITING PRODUCTS

CROSS REFERENCE TO RELATED APPLICATION

This application is a divisional of copending applications application Ser. No. 07/905,132, filed Jun. 23, 1992 now U.S. Pat. No. 5,965,414; which is a continuation of Ser. No. 07/468,575, filed Jan. 23, 1990, abandoned, which is a continuation of Ser. No. 07/082,118, filed Aug. 6, 1987, now abandoned, which is a continuation-in-part of Ser. No.06/794,468, filed Nov. 4, 1985, now U.S. Pat. No. 4,956,177.

BACKGROUND OF THE INVENTION (1) Field of the Invention

The present invention relates to yeast and mold (fungus) inhibiting products produced by Lactobacillus species, particularly a *Lactobacillus casei* having the essential identification characteristics of *Lactobacillus casei* var. *rhamnosus* NRRL-B-15972. In particular, the present invention relates to a process for producing the products and to their use in preventing yeast and mold growth in foods and other materials.

(2) Prior Art

Various substances are produced by microorganisms which are antimicrobial in character. Lactobacillus are known to produce metabolic products that are antibacterial and allow them to compete more effectively in certain environments. It is not believed to be known that lactobacilli produce any separately isolatable metabolic products which inhibit yeast and mold.

OBJECTS

It is therefore an object of the present invention to provide novel Lactobacillus metabolic products which inhibit yeast and mold and which are referred to herein as "FIC" or fungal inhibiting compounds. Further it is an object of the present invention to provide a process for producing the FIC products as well as a method for using these FIC products in foods and other materials. These and other objects will become increasingly apparent by reference to the following description.

GENERAL DESCRIPTION

The present invention relates to a process for producing yeast and mold inhibiting products (FIC) which comprises: incubating live cells of a Lactobacillus species in a nutrient medium for the cells including a sulfur containing organic compound (preferably cysteine, garlic extract, whey, yeast, yeast extract, molasses or protein digest) which induces the formation of the products (FIC), a protein source, and a carbon source, so as to produce an isolatable amount of the products (FIC) in the nutrient medium, wherein the products (FIC) inhibit *Penicillium oxalicum* spores in an assay with the products (FIC) and the *Penicillium oxalicum* spores mixed.

The present invention relates to a process for producing yeast and mold inhibiting products (FIC) which comprises: incubating live cells of a Lactobacillus species in a nutrient medium containing growth factors present in cysteine, garlic extract, milk, whey, yeast, yeast extract, molasses or protein digest which induce the formation of the products (FIC), a protein source and a carbon source, so as to produce the products (FIC) in the nutrient medium; and treating the nutrient medium which has been incubated so as to produce the products (FIC) with or without the live cells, wherein the products (FIC) inhibit Penicillium oxalicum spores in an assay with the products (FIC) and the *Penicillium oxalicum* spores mixed.

Further still the present invention relates to a process for producing yeast and mold inhibiting products (FIC) which comprises: incubating live cells of a Lactobacillus having yeast and mold inhibiting characteristics of *Lactobacillus casei* var. *rhamnosus* NRRL-B-15972 in a nutrient medium for the cells containing growth factors present in cysteine, garlic extract, milk, whey, yeast, yeast extract, molasses or protein digest which induce the formation of the products (FIC), and a carbon source so as to produce products (FIC) in the nutrient medium wherein the products (FIC) inhibit *Penicillium oxalicum* spores in an assay with the products (FIC) and the *Penicillium oxalicum* spores mixed; and treating the nutrient medium which has been incubated so as to produce the products (FIC) with the cells disrupted.

Finally the present invention relates to a method for preventing yeast and mold growth in a material in need thereof which comprises: adding to the material products (FIC) produced by a process which comprises incubating live cells of a Lactobacillus in a nutrient medium containing a sulfur containing organic compound, a protein source and a carbon source which induce the formation of the yeast and mold inhibiting products (FIC) in the nutrient medium wherein the products (FIC) inhibit *Pencillium oxalicum* spores in an assay with the products (FIC) and the *Penicillium oxalicum* spores mixed and then treating the nutrient medium which now contains live cells, in such a manner so as to produce the final products (FIC) in a form containing live cells, dead cells or no cells to thereby prevent yeast and mold growth in the material.

The preferred products (FIC) from *Lactobacillus casei* var. *rhamnosus* NRRL-B-15972 have a molecular size of less than 1000 daltons and an ultraviolet absorbance at 269 nanometers. It is a complex mixture of compounds.

*Lactobacillus casei* var. *rhamnosus* NRRL-B-15972 is described in application Ser. No. 794,468. It is deposited with the Northern Regional Research Laboratory in Peoria, Ill. Any Lactobacillus strain, whether naturally occurring or genetically engineered, with genetic material (in chromosomes or plasmids) encoding for similar yeast and mold inhibiting products (FIC) can be used to produce the products (FIC), although *Lactobacillus casei* var. *rhamnosus* NRRL-B-15972 appears to be the most effective naturally occurring (non-genetically engineered) source.

Various growth media for Lactobacillus can be used. The media must promote growth of cells and production of the products (FIC). Media to promote growth must contain protein and a carbon source. In addition, for products (FIC) production the media preferably includes a sulfur containing organic compound. Preferably the growth media include a sulfur containing organic compound, a protein source, a carbon source and minerals. Proteinaceous or amino acid materials from natural sources can include the sulfur containing compound. Thus protein sources such as milk, whey, yeast, yeast extract or protein digest can be a source of the sulfur compound and stimulate the production of the products (FIC). Separate compounds containing sulfur without being a protein source, such as garlic extract and cysteine, can be used. The carbon source can include fructose, sucrose, dextrose, lactose or molasses. Minerals which facilitate growth of the cells, such as manganese and magnesium salts are available in corn steep liquor or can be added as pure salts. Preferably buffers such as alkali metal phosphates are used to maintain the pH. It has been found that cinnamic acid and/or an alkali metal propionate and/or phenylalanine further stimulate the production of the yeast and mold inhibitory products (FIC) in the above referenced media. Preferably the cells are grown at a temperature between 10° and 50° C. Numerous variations of the nutrient medium and growth conditions will occur to those skilled in the art.

After growth of the cells, the nutrient medium preferably is processed to eliminate most of the live cells and then either concentrated or extracted to produce the yeast and mold inhibiting products (FIC). The yeast and mold inhibiting products (FIC) can be dried, lyophilized or frozen prior to use. The preferred process for producing the products (FIC) in a relatively unconcentrated form is spray drying the growth medium after the yeast and mold inhibitory products are produced in the medium. All of these methods are well known to those skilled in the art.

Various water immiscible solvents can be used to extract the products from the growth medium, such as lower alkyl alcohols and esters. Preferably n-butanol isopropanol, acetone, ethyl acetate or ethanol and combinations with water are used. The products can also be separated by chromatographic methods including molecular sieve, ion exchange and high pressure liquid chromatography methods well known to those skilled in the art. Impurities can be removed from the products (FIC) using molecular sieves and reverse osmosis. Essentially any chemical and/or mechanical process can be used for the separation.

As used herein, the term "material" means any surface in need of treatment by the FIC. The term material includes living and non-living surfaces. The yeast and mold inhibiting products (FIC) are preferably used in foods in an amount which inhibits P. oxalicum for at least 72 hours. The amount of FIC used depends upon the number of yeast and mold cells in the material to be treated.

Any food can be preserved by the method of the present invention especially carbonated beverages, Cottage cheese, yogurt, margarine, bread, grains and nuts. Because the products (FIC) are effective in a broad pH range pH 3 to 10 they are especially useful for use to preserve any food by the method of the present invention. The yeast and mold inhibiting products (FIC) are particularly useful in fermented foods and other preserved foods which are prone to such spoilage. Other food applications include silage and corn mold treatment and peanut treatment to prevent aflatoxin contamination by mold. Various materials can be treated and FIC can be used to prevent infection by mold and yeast, including living tissue as the material either in culture or in an animal, particularly mammals. Topical application of FIC to mammals either internal or external is preferred. Detergents, soaps and other cleansers can be combined with the products (FIC).

SPECIFIC DESCRIPTION

Summary of Examples

Lactobacillus casei var. rhamnosus NRRL-B-15972 produces products (FIC) which inhibit a wide variety of yeasts including: P. camemberti, B. allii, Caldosporium, Debaromyces sp., S. cerevisiae (Baker's) and molds. The compounds in the products (FIC) are polar and have a molecular size of less than 1,000 daltons and are not proteins, or lipids. The product (FIC) is unique in that it is insoluble in chloroform and n-hexane, and soluble in ethanol, n-butanol and acetone. The FIC appears to be temperature stable, i.e. −70° C. to +100° C., however it is destroyed by autoclaving at 121° C. FIC is stable from pH 3–10. Nutritional studies indicate that alkali metal propionate, phenylalanine, and/or cinnamic acid appear to further stimulate production of the yeast and mold inhibiting products by Lactobacillus casei var. rhamnosus as well as by other Lactobacilli. Purification of the products (FIC) can be obtained through the use of organic extraction and flash evaporation. The following examples show the method of production and use of the yeast and mold inhibiting products (FIC) of the present invention.

EXAMPLE 1

Lactobacillus sp. Exhibiting antifungal Activity.

Antifungal products (FIC) are produced by Lactobacillus having various degrees of activity. These are shown in Table 1 wherein various cultures grown on agar were tested against P. oxalicum spores.

TABLE 1

| | Fic Zone 48h[1] |
|---|---|
| Lactobacillus casei var. rhamnosus NRRL-B-15972 | 5.0 mm |
| L. casei var. casei 2610 | 3.0 mm |
| L. casei var. casei 2601 | 4.0 mm |
| L. casei var. tolerans | 4.0 mm |
| L. casei VH | 4.0 mm |
| L. plantarum ATCC 8014 | 4.0 mm |
| L. acidophilus SFS[2] | No Zone Produced |
| L. bulgaricus YB-1[2] | 2.0 mm |
| L. bulgaricus DFW[2] | 3.0 mm |
| L. bulgaricus LBHW[2] | 3.0 mm |
| L. bulgaricus HCOYWC[2] | 3.0 mm |
| L. parma | No Zone Produced |

(1) The Cells were grown 24h at 35° C. on MRS agar medium (DIFCO, Detroit, Michigan). MRS™ contains yeast extract along with proteose peptone, beef extract, sodium acetate, sodium citrate and dextrose. Agar is added to form a gel. The live cells were then overlayed on the agar with $10^6$ spores/ml of the fungus Penicillium oxalicum. The width of the clear zone was measured.
(2) These cultures were grown in a confined chamber @ 35° C. with carbon dioxide and then challenged with the P. oxalicum. The L. bulgaricus and L. casei strains listed in Table 1 have different genetic and physiological characteristics. All of the strains are on deposit at Microlife Technics, Inc., Sarasota, Fla.

None of the Lactobacilli were as effective as L. casei var. rhamnosus NRRL-B-15972. This strain was used for the subsequent Examples.

EXAMPLE 2

Preparation, production and purification of liquid yeast and mold inhibiting products (FIC).

Medium Incubation—A culture of Lactobacillus casei var. rhamnosus NRRL-B-15972 was grown in MRS™ broth (Difco, Detroit, Mich.) supplemented with 1% by weight yeast extract (Oxoid®, Oxoid Ltd., Basingstoke, Hampshire, England). MRS™ contains yeast extract, proteose peptone, beef extract, sodium acetate, sodium citrate, and dextrose in a broth. One (1) liter of the medium was sterilized, inoculated with the culture and incubated at 35° C. without shaking or neutralization for 18 hours.

The purification procedure was:
1. Flash Evaporation—The cells and medium were concentrated (1 liter to 100 ml) using a flash evaporator (Roto-Vap™). A dark brown mixture remained (100 ml).

2. Butanol—The concentrated cells-medium suspension was then mixed with 1 liter of n-butanol. This mixture was placed in a separatory funnel and separation occurred in 30 minutes. The bottom water layer was discarded. The upper layer (n-butanol layer) was then concentrated using the flash evaporator until a dry particulate material remained. This material was then resuspended in 50 ml of distilled water.

3. Ethanol Extraction—To the 50 ml of distilled water mixture, 250 ml of ethanol (100%) was added and impurities were allowed to precipitate overnight at −70° C. After precipitation had occurred, the solution was centrifuged at −20° C. for 20 minutes at 12,000 ×g. The supernatant was then concentrated on the flash evaporator. The oily material was resuspended in 10 to 20 ml of distilled water.

4. Column Chromatography—A Pharmacia column (2.6 cm×35 cm) containing 125 g of silica gel (Sigma™, St. Louis Miss.). 28–200 mesh, 22 Angstrom mean pore diameter) was prepared. The silica gel was suspended in methanol, chloroform and ethyl acetate in a ratio of 1:2:3 respectively. The total column volume was 186 ml. Approximately 5 ml of the concentrated ethanol fraction was loaded onto this column. The column was washed with approximately 400 ml of the above solvent. The column washings were discarded.

The column was then washed with a mixture of water, 5% ammonium hydroxide, glacial acetic acid, acetone and n-butanol as in a ratio of respectively 2:3:3:5:7 as a solvent. The solvent was collected in 5 ml fractions. The 20th through 30th fractions which contained the antifungal substance were saved. These fractions were collected and concentrated using the flash evaporator and then resuspended in 5 ml of distilled water.

5. Acetone Precipitation—To 5 ml of the concentrated column material, 150 ml of acetone was added and precipitation was allowed to occur overnight at −70° C. to remove impurities. The supernatant was centrifuged, the acetone was flash evaporated on the flash evaporator and the resulting antifungal substance was resuspended in 3 ml of distilled water. FIC was assayed using a) MRS (Difco) agar plates; b) MRS (Difco) soft agar, (1 g of Bacto™ (Difco) agar per 100 ml MRS broth) at 8 ml/plate tempered at 55° C.; c) Penicillium oxalicum spores $10^8$/ml in distilled water, at 1 ml per assay; and d) The material to be assayed. Eight (8) ml of soft agar was combined with 1 ml of the spores ($10^8$/ml) and 1 ml of assay material, the mixture was vortexed and the contents were poured over an MRS plate and then incubated at 25° C. The plates then were examined for fungal growth. There is either growth or no growth on the plate. The degree of growth is rated between +1 and +4 as described hereinafter. The final purified product resulted in no growth of *P. oxalicum* after 96 hours.

EXAMPLE 3

This example shows an alternate extraction method for producing an FIC similar to Example 2.

Medium and Incubation—The culture was grown in Folic Acid Assay Medium (DIFCO, Detroit, Mich.) supplemented with 1 yeast extract (OXOID®) or 1% whey protein concentrate or 1% garlic extract. One liter of the medium was sterilized, inoculated with culture and incubated at 35° C. for 18 hours without shaking or neutralization.

The purification procedure was:

1. Butanol Extraction—The cells and medium suspension were mixed with 5 liters of n-butanol. The mixture was placed in a separatory funnel and the n-butanol layer was saved. This layer was then concentrated using the flash evaporator.

2. Ethanol Extraction—The above mixture (50 ml) was combined with 250 ml of ethanol (100%) and precipitated overnight at −70° C. The material was centrifuged at −20° C. for 20 minutes at 12,000 ×g. The supernatant was then decanted and concentrated using the flash evaporator.

3. Dialysis—The ethanol precipitate was then placed in a dialysis bag with 1000 dalton molecular size cut off. The bag and its contents were then dialyzed against distilled water (100 ml) at 4° C. for 18 h. The distilled water was then concentrated on the flash evaporator. FIC was assayed as in Example 2. The results are shown in Table 2.

TABLE 2*

| Growth Period | Folic Acid Assay Medium Unsupplemented | Folic Acid Assay Medium plus 1% yeast extract | Folic Acid Assay Medium Plus 1% Whey Protein Concentrate | Folic Acid Assay Medium Plus 1% Garlic Extract |
|---|---|---|---|---|
| 24 h | +1 | — | — | — |
| 48 h | +2 | +1 | — | — |
| 96 h | +4 | +2 | +1 | — |

*assayed as in Example 2 with a spore concentration of $10^7$ spores per ml.
— = no mycellial masses present.
+1 = mycellial masses present, greater than 1000.
+2 = confluent white lawn.
Folic acid based assay medium supplemented with 1% garlic extract produced the highest concentration of FIC.

EXAMPLE 4

Comparison of the Expression of FIC by *L. casei* var. *rhamnosus* NRRL-B-15972 In Various Nutrient Media.

*Lactobacillus casei* var. *rhamnosus* NRRL-B-15972 was inoculated into 250 ml of various nutrient media and incubated at 35° C. for 18 hours. The cells and media were then extracted and processed as previously described in Example 2. One ml of extracted material was then assayed using the fungal biological method of Example 2, and with aL spore concentration of $10^7$ spores per ml. The assay plates were examined for fungal growth after 24 hours, 48 hours and 72 hours incubation, respectively. The results are shown in Table 3.

TABLE 3

| | Incubation Time | | | |
|---|---|---|---|---|
| Medium | 24 h | 48 h | 72 h | |
| Control uninoculated MRS broth (Difco ®) supplemented with 1% yeast extract (Oxoid ®). | +1 | +4 | +4 | * |
| MRS Broth (Difco ®). | — | +2 | +4 | |
| Whey based broth supplemented with 1% yeast extract (Oxoid ®). | +1 | +4 | +4 | |
| MRS broth (Difco ®) supplemented with 1% yeast extract (Oxoid ®) | — | — | +1 | |

TABLE 3-continued

| Medium | Incubation Time | | |
|---|---|---|---|
| | 24 h | 48 h | 72 h |
| MRS broth (Difco ®) supplemented with 1% yeast extract (Tureen ®) | — | +1 | +2 |
| MRS broth (Difco ®) supplemented with 0.01% sodium propionate | — | — | — |
| MRS broth (Difco ®) supplemented with 0.01% cinnamic acid | — | — | — |
| MRS broth (Difco ®) supplemented with 0.01% phenylalanine | — | — | — |
| Corn steep based medium including 4% Corn steep, 5% lactose, 0.01% sodium propionate, 0.2% sodium citrate, 1.0% Edamin (enzymatic digest of lactalbumin) S (Kraft, Sheffield Products, Kraft, Inc., Norwich, N.Y.) | — | +1 | +1 |

\*
— = No mycellial masses present.
+1 = Mycellial masses present greater than 1000.
+2 = Confluent white lawn.
+3 = Confluent lawn piled in mass.
+4 = Confluent lawn pigments green.

The above results indicate that the selection of the nutrient medium is important for production of the products (FIC). Even when a whey based medium was supplemented with yeast extract to obtain good Lactobacillus cell growth, sufficient products (FIC) were not produced. Also, the above results indicate that not only are the medium ingredients important for the products (FIC) production, but the brand of a particular ingredient also is important. If Oxoid® yeast extract in the medium was substituted with another brand of yeast extract, Tureen®, expression of the products (FIC) was reduced. The MRS Difco® medium supplemented with 1% Oxoid® yeast extract. produced the highest level of the products (FIC) production and thus the best fungal inhibition. Cinnamic acid, phenylalanine and sodium propionate all enhanced production of FIC.

EXAMPLE 5

Preparation and Production of Dried FIC For Food Application. *Lactobacillus casei* var. *rhamnosus* NRRL-B-15972 was grown in broth consisting of the following components: 2% lactose, 1% nonfat dry milk, 1% yeast extract, 0.36% $Na_2HPO_4$, 0.56% $KH_2PO_4$ and trace amounts of $MgSO_4$ and $MnSO_4$. The inorganic salts $Na_2HPO_4$ and $KH_2PO_4$ were made ten (10) times more concentrated than necessary and then added to the growth medium after autoclaving. One (1) liter of the medium was sterilized at 121° C. for 15 minutes inoculated with the culture and incubated at 35° C. without shaking for 18 hours.

After the culture was grown 18 hours at 35° C. in the above medium, the culture flask was then placed in a 70° C. incubator for 45 minutes, to heat inactivate the culture. The nutrient medium was then lyophilized 18 hours. From 25 ml of liquid nutrient medium, 1.2 g of dried products (FIC) was obtained.

The titration of the dried products (FIC) with a constant fungal concentration of $10^7$ *P. oxalicum* spores per ml, as in Example 2, is shown in Table 4.

TABLE 4

| Growth Period | Amount of dried products (FIC) (g/ml) | | | | | Control |
|---|---|---|---|---|---|---|
| | 0.3 | 0.4 | 0.6 | 1.2 | 2.4 | 0.0 |
| 24 h | — | — | — | — | — | + |
| 48 h | +3 | +3 | +3 | +1 | — | +3 |
| 72 h | +4 | +4 | +4 | +3 | — | +4 |

— = means no mycellial masses present
+1 = visible mycellial masses
+2 = white lawn of mycellial masses
+3 = white dented lawn of mycellium
+4 = final green pigmentation of mycellium Titration of 1 g of the dried products (FIC) with a variable number of fungal spores at 25° C. is shown in Table 5.

TABLE 5

| Growth Period | Number (of spores per ml) | | | | Media Control | FIC Control | Fungus Control[a] |
|---|---|---|---|---|---|---|---|
| | $10^7$ | $10^6$ | $10^5$ | $10^4$ | | | |
| 24 h | — | — | — | — | — | — | +1 |
| 48 h | +2 | +2 | +1 | — | — | — | +2 |
| 72 h | +4 | +4 | +4 | +1 | — | — | +4 |

+1 = visible mycellial masses
+2 = white lawn of mycellial masses
+3 = white dented lawn of mycellium
+4 = final green pigmentation of mycellium
[a] $10^7$ spores per ml The above results indicate that a dried non-extracted FIC preparation exhibits fungal inhibition.

EXAMPLE 6

Use of Dried Products (FIC) to Extend the Shelf Life of Cottage cheese.

The products (FIC) of Example 5 was sprayed onto surface of Cottage cheese and $10^5$ *P. oxalicum* spores per ml were added to the Cottage cheese. The products (FIC) were used in a concentration of 1.0 gram per ml. About 35 grams of Cottage cheese were used per test. The tests were conducted at 25° C. The results are shown in Table 6.

TABLE 6

| Growth Period | Cottage cheese without FIC and added fungus | Cottage cheese with added fungus only | Cottage cheese with FIC only | Cottage cheese with added fungus and Dried FIC |
|---|---|---|---|---|
| 24 h | — | — | — | — |
| 48 h | — | — | — | — |
| 72 h | — | — | — | — |
| 96 h | — | +4 | — | — |

— = no mycellial masses present.
+4 = final green pigmentation of mycellium, not edible.

The products (FIC) of the present invention will inhibit up to $10^7$ spores per ml of *Penicillium oxalicum* for at least 24 hours in the least concentrated form. The products (FIC) will easily inhibit up to $10^3$ spores per ml which is a very significant mold population in a material. A mold population of greater than 10 per ml is significant.

It is intended that the foregoing description be only illustrative of the present invention and that the present invention be limited only by the hereinafter appended claims.

We claim:

1. A method for inhibiting yeast and mold growth in a material in need thereof which comprises:
   (a) adding to the material an effective amount to inhibit mold and yeast growth in the material of a product produced by a process which comprises incubating live cells of a Lactobacillus having all of the identifying characteristics of *Lactobacillus casei* var. *rhamnosus* NRRL-B-15972 in a nutrient medium containing a sulfur containing organic compound, a protein source and a carbon source, which induce the formation of a yeast and mold inhibiting product in the nutrient medium, wherein the product in the nutrient medium inhibits *Penicillium oxalicum* spores in an assay with the product and the *Penicillium oxalicum* spores mixed; and
   (b) treating the nutrient medium which contains live cells, so as to produce the product in a form containing live cells, dead cells or no cells, wherein the product is polar, non-protein, non-lipid, has a molecular size of less than 1000 daltons, insoluble in chloroform or hexane and soluble in butanol and acetone, is temperature stable at −70° C. to 100° C. and is stable at a pH between 3 to 10.

2. The method of claim 1 wherein the material is a food.

3. The method of claim 2 wherein the food is a carbonated beverage, Cottage cheese, yogurt, margarine, bread, grains or nuts.

4. The method of claim 1 wherein the material is a cleanser.

5. Yeast and mold growth inhibiting product prepared by a process which comprises:
   (a) incubating live cells of Lactobacillus having all of the identifying characteristics of *Lactobacillus casei* var. *rhamnosus* NRRL-B-15972 in a nutrient medium for the cells containing effective amounts of a sulfur containing organic compound and of a carbon source so as to produce an isolatable amount of the product in the nutrient medium; and
   (b) recovering the product from the nutrient medium, wherein the polar, non-protein, non-lipid, has a molecular size of less than 1000 daltons, insoluble in chloroform or hexane and soluble in ethanol, in butanol and acetone, is temperature stable at between −70° C. and 100° C. and is stable at a pH between 3 to 10.

6. The product of claim 5 wherein the nutrient medium which is incubated contains the yeast extract for the growth factors, non-fat dry milk as the protein source; lactose, sucrose, dextrose, fructose or molasses as the carbon source and corn steep liquor as a source of minerals.

7. The product of claim 5 wherein the nutrient medium contains a compound selected from the group consisting of cinnamic acid, an alkali metal propionate and phenylalanine, in an amount which increases the production of the production of the product by the process.

8. The process of claim 5 wherein in step (b) the nutrient medium with the live cells is dried.

9. Yeast and mold growth inhibiting product prepared by a process which comprises:
   (a) incubating live cells of a Lactobacillus having all of the identifying characteristics of *Lactobacillus casei* var. *rhamnosus* NRRL-B-15972 in a nutrient medium for the cells containing effective amounts of growth factors present in a composition selected from the group consisting of cysteine, garlic extract, milk, whey, yeast, a yeast extract, molasses and a protein digest which induce the formation of the products (FIC), a protein source and of a carbon source to thereby produce isolatable amounts of the product in the nutrient medium; and
   (b) treating the nutrient medium which has been incubated to recover the product by removal of water from the nutrient medium to produce the product and nutrient medium in admixture, wherein the product is polar, non-protein, non-lipid, has a molecular size of less than 1000 daltons, are insoluble in chloroform or hexane and soluble in ethanol, in butanol and acetone, are temperature stable at between −700° C. and 100° C. and are stable at a pH between 3 to 10.

10. The product of claim 9 wherein in step (b) the nutrient medium is lyophilized.

11. The product of claim 9 wherein the Lactobacillus is incubated in the nutrient medium at a temperature of between about 100° C. and 500° C.

12. The product of claim 9 wherein the nutrient medium contains lactose, sucrose, dextrose, fructose or molasses as the carbon source and corn steep liquor as a source of minerals.

13. The product of claim 12 wherein the nutrient medium contains in addition a manganese salt, a magnesium salt and an alkali metal phosphate.

14. A yeast and mold inhibiting product prepared by a process which comprises:
   (a) incubating cells of a Lactobacillus having all of the identifying characteristics of *Lactobacillus casei* var. *rhamnosus* NRRL-B-15972 in a nutrient medium for the cells containing effective amounts of growth factors present in compositions selected from the group consisting of cysteine, garlic extract, milk, whey, yeast, a yeast extract, molasses and a protein digest and of a carbon source so as to produce the product in the nutrient medium;
   (b) mixing the incubated nutrient medium with an organic solvent which extracts the product into the solvent;
   (c) separating the solvent with the extracted product from the nutrient medium; and
   (d) separating the product from the solvent, wherein the product is polar, non-protein, non-lipid, has a molecular size of less than 1000 daltons, is insoluble in chloroform or hexane and soluble in ethanol, in butanol and acetone, is temperature stable at between −700° C. and 100° C. and is stable at a pH between 3 to 10.

15. The product of claim 14 wherein the solvent mixture is cooled to thereby precipitate impurities which are removed.

16. The product of claim 14 wherein in addition the separated product is purified to separate impurities using liquid chromatography.

17. The product of claim 14 wherein in addition the product is purified by liquid dialysis which passes compounds through a membrane having a molecular size of about 1000 or less and wherein the product is passed through the membrane and collected.

18. The product of claim 19 wherein in addition the purified product is further purified by liquid chromatography using a solvent mixture to produce separation of the product from impurities.

19. The product of claim 18 wherein in addition the product without the impurities is subjected to a further purification using liquid chromatography.

20. The product of claim 14 wherein the nutrient medium contains the yeast extract and the protein digest.

21. The product of claim 14 which has a primary ultraviolet absorbance at about 269 nanometers.

* * * * *

UNITED STATES PATENT AND TRADEMARK OFFICE
CERTIFICATE OF CORRECTION

PATENT NO.    : 6,277,374 B1
DATED         : August 21, 2001
INVENTOR(S)   : Peter A. Vandenbergh and Stephen W. King It is certified that error appears in the above-identified patent and that said Letters Patent is hereby corrected as shown below:

<u>Title page,</u>
Item [54], the Title should read as follows: -- **PROCESS FOR PRODUCING YEAST AND MOLD INHIBITING PRODUCTS BY CULTURING *LACTOBACILLUS CASEI VAR. RHAMNOSUS* --**.

<u>Column 5,</u>
Line 64, "of 1 yeast" should be -- of 1% yeast --.

<u>Column 6,</u>
Line 47, "a L spore" should be -- a spore --.

<u>Column 9,</u>
Line 40, "wherein the polar, non-protein" should be -- wherein the product is polar, non-protein --.

<u>Column 10,</u>
Line 10, "between $-700^\circ$C and" should be -- between $-70^\circ$C and --.
Line 42, "between $-700^\circ$C and" should be -- between $-70^\circ$C and --.
Line 55, "product of Claim 19" should be -- product of Claim 17 --.

Signed and Sealed this

Twenty-fifth Day of June, 2002

*Attest:*

JAMES E. ROGAN
*Attesting Officer*    *Director of the United States Patent and Trademark Office*